(12) United States Patent
Vuorinen (10) Patent No.: US 6,958,108 B1
(45) Date of Patent: Oct. 25, 2005

(54) METHOD OF PRODUCING A FIBER PRODUCT HAVING A STRENGTH SUITABLE FOR PRINTING PAPER AND PACKAGING MATERIAL

(75) Inventor: Tapani Vuorinen, Espoo (FI)

(73) Assignee: M-real Oyj, Espoo (FI)

( * ) Notice: Subject to any disclaimer, the term of this patent is extended or adjusted under 35 U.S.C. 154(b) by 0 days.

(21) Appl. No.: 09/674,289

(22) PCT Filed: Apr. 30, 1999

(86) PCT No.: PCT/FI99/00359

§ 371 (c)(1),
(2), (4) Date: Oct. 30, 2000

(87) PCT Pub. No.: WO99/57370

PCT Pub. Date: Nov. 11, 1999

(30) Foreign Application Priority Data

Apr. 30, 1998 (FI) ...................................... 980968

(51) Int. Cl.[7] .................. D21C 17/20; D21C 17/21; D21C 17/25
(52) U.S. Cl. ........................ 162/9; 162/78; 162/177; 106/162.5
(58) Field of Search ................. 162/24, 65, 71, 162/78, 164.1, 9, 175, 158, 176, 134, 177; 106/162.5

(56) References Cited

U.S. PATENT DOCUMENTS

| | | | |
|---|---|---|---|
| 3,674,621 A | * | 7/1972 | Miyamoto et al. .......... 162/146 |
| 3,719,552 A | * | 3/1973 | Farley et al .................. 162/65 |
| 4,710,270 A | * | 12/1987 | Sunden et al. .............. 162/175 |
| 5,354,424 A | * | 10/1994 | Rha et al. .................. 106/162.5 |
| 5,637,193 A | * | 6/1997 | Hassi et al. .................. 162/175 |
| 6,165,320 A | * | 12/2000 | Bates et al. .................. 162/135 |

FOREIGN PATENT DOCUMENTS

| | | |
|---|---|---|
| EP | 0 273 075 A1 | 7/1998 |
| GB | 1110004 | 4/1968 |
| GB | 1111165 | 4/1968 |
| GB | 1504128 | 3/1978 |
| JP | 9-132896 A | 5/1997 |
| JP | 9-291490 A | 11/1997 |
| JP | 10-1897 A | 1/1998 |
| WO | WO 96/33310 | 10/1996 |

OTHER PUBLICATIONS

Derwent Accession No. 98-603601, UNI-CHARM KK: "Hydrolytic sheet—includes base material sheet of water-dispersive fibre, and carboxyl methyl cellulose and/or its salt; and a liquid component"; & JP, A, 10273892, 981013.

* cited by examiner

Primary Examiner—Steve Alvo
(74) Attorney, Agent, or Firm—Kubovcik & Kubovcik (57) ABSTRACT

The present invention relates to a modified fiber product and a method of producing same. According to the method, the cellulosic raw material is formed into a fiber suspension, into which components modifying the properties of the fibers are added, subsequent to which the fibrous material is dried in connection with, for example, web forming. According to the invention, alkyl derivative of cellulose is mixed into the fiber suspension in alkaline conditions, the derivative being at least partly dissolved in water, and the derivative is allowed to be sorbed into the fibrous material prior to drying such that the sorbed cellulose derivative can not be washed off with water. The strength properties or the water retention of paper and paperboard products can be improved by using the invention.

20 Claims, 4 Drawing Sheets

METHOD OF PRODUCING A FIBER PRODUCT HAVING A STRENGTH SUITABLE FOR PRINTING PAPER AND PACKAGING MATERIAL

The present invention relates to a method according to the preamble of claim 1 for producing a fiber product. According to the method, a cellulosic raw material is formed into a fiber suspension, into which components modifying the properties of the fibers are introduced, subsequent to which the suspension is dried.

The invention is especially related to a method of producing a web having good strength properties and a high water absorption capability.

The invention also relates to a fiber product as described in the preamble of claim 21.

It is known in prior art that the properties of the cellulose fibers used for producing paper can be modified by adding polymers to the fiber suspension (pulp) prior to wire forming. Suitable additive materials include starch-based components, such as cationed starch, and different kinds of plastic materials, such as polyacryl polymers and polyamineamide-, polyamine- and acrylamino-epichlorohydrine polymers. Conventionally, the amounts added are about 0.5–5% (by weight) of the pulp dry material.

The above-mentioned polymers can be used for increasing the dry and wet strength and water absorption of papers. A drawback of the known methods is, however, the relatively weak bonding between the conventional polymers and the cellulose fibers. For this reason the materials accumulate in the water circulation of the paper machine, which causes additional problems in treating and cleaning white water. Another drawback of the synthetic materials is their bad biodegradability, which affects the recycling and composting of the paper manufactured from the pulp.

Anionic polymers containing carboxyl groups or carboxylate ions in the form of alkali metals or ammonium salts are often added to the pulp to improve the retention of the cationic polymers. Carboxyalkylated polysaccharides, such as carboxymethyl cellulose, CMC (see for example U.S. Pat. Nos. 5,061,346 and 5,316,623) can especially be mentioned as examples of anionic polymers. Usually, these polymers are added to the pulp in larger quantities than the usual modifying chemicals, i.e. the amount is typically about 5–20% of the fiber material content of the pulp.

A drawback of the mixing of cationic and anionic polymers is that they might react together and macrocoagulate, if they are added together or if the anionic polymer is introduced to the fibers before the cationic modifying chemicals. For this reason it is difficult to evenly distribute the cationic polymer in the fibers. Additionally, using several different components will further affect the treatment of white water.

There are also prior art solutions, in which the strength properties of papers are enhanced by adding mainly only alkyl derivatives of cellulose as modifying agents. The GB patent publication 978 953 describes a method of forming a fiber web having good strength properties, according to which method a hydrophilic bonding compound is produced from cellulose ether, which is then mixed with the pulp or water phase either in swollen form or as a gel. The amount of bonding compound added to the pulp can be as high as 25% of the amount of pulp. According to the above patent publication, the method produces very even sheets, and the bonding compound increases the bonds between the fibers, thus increasing the strength of the sheet.

However, the solution is a complex one and difficult to apply on an industrial scale, because the cellulose ether will first have to be extruded for forming a bonding compound having a suitable composition.

U.S. patent publication No. 5,275,698 describes a method of adding cellulose polymers to the pulp. The cloud point of the utilized cellulose polymers is between 10–95° C., and their solubility is inversely proportional to the temperature. When the polymer is added as water solution to the pulp in a temperature below the cloud point, the temperature of the pulp being higher than the cloud point of the polymer, the polymer is caused to coagulate into a colloid as it is dispersed into the pulp.

In the method according to the US patent publication the coagulation of the polymers is difficult to control, and during introduction the pulp must be vigorously agitated in order to uniformly distribute the polymer into the fibers.

The present invention relates to a method of removing the drawbacks associated with the prior art and to achieve a totally novel solution for modifying the properties of cellulose fibers. The invention especially relates to a method of bonding the cellulose derivative, especially a derivative of alkylated cellulose, such as carboxymethyl cellulose, to the fibers of the cellulose pulp even without any retention enhancers so that the cellulose derivative can not be washed off.

The present invention is based on the idea that an alkyl derivative of cellulose in at least partially water-soluble form is added to the pulp in alkali conditions, and that the derivative is allowed to bond into the fibrous raw material prior to drying in connection with e.g. web forming. The bonding (sorption) is secured by allowing the cellulose derivative to contact the cellulose for a sufficient period of time.

When using CMC as the cellulose derivative, the modified fiber product according to the invention will contain at least 0.1% of bonded CMC by (dry) weight of the fibers, the DP of which is about 100–5000 and DS about 0.1–0.4.

More specifically, the method according to the invention is mainly characterized by what is stated in the characterizing part of claim 1.

The fiber product according to the invention, on the other hand, is characterized by what is stated in the characterizing part of claim 21.

The solution according to the invention will accomplish considerable advantages. Thus, the strength properties of paper manufactured from cellulose pulp according to the invention can be considerably increased. Increase of internal bond strength (the density of the sheet remains constant) shows an increase of specific bond strength. Tensile strength and stretch at break are accordingly increased. Therefore, pulps produced according to the invention can be used in all applications, in which the strength of paper is of importance. Sorption of cellulose derivative, such as CMC, can reduce the grammage and/or the amount of strengthening mixture.

Another considerable application for pulps produced according to the invention are soft tissues, in which the bonded cellulose derivative will increase water retention.

The invention can also be used for producing modified fiber products that, on account of their good water retention, can be used in hygiene products, such as diapers.

According to the invention, the sorption can be even achieved essentially without separate retention chemicals, even though they can also be used. Preferably, an amount in excess of 50% of the cellulose derivative in the solution will be bonded into the fibers.

In the following, the invention will be discussed in more detail using a detailed description of the invention and some working examples.

BRIEF DESCRIPTION OF THE DRAWINGS

The following drawings graphically illustrate test results of pulps treated with CMC and, correspondingly paper sheets made from these pulps, in which.

The invention is exemplified by using carboxymethyl cellulose and its sorption into cellulose pulp as an example. Even though CMC represents an especially preferred embodiment, it is to be noted, that the principles described in the invention can also be applied for other cellulose derivatives, such as methyl cellulose, hydroxyethyl cellulose and hydroxypropyl cellulose, that are similar in the respect of bonding. The properties, for example strength and/or water absorption, of cellulose fibers can be modified by means of these derivatives.

In the examples described below, the solution according to the invention is used for modifying the fibers of chemical pulp. In this context, chemical pulp means pulp that has been treated with cooking chemicals for delignifying the cellulose fibers. According to an advantageous embodiment of the invention, the invention is applied to pulps produced with sulphate process and other alkaline processes. "Sulphate process" in this context means a cooking method in which the main cooking chemicals are sodium sulphide and sodium hydroxide. Extended cooking, in which a conventional sulphate process is continued until the kappa value of the pulp is below 20, can be mentioned as an example of other alkaline processes. Typically, these methods include oxygen treatment. The invention can as well be used for modifying the properties of pulps produced with acid cooking methods. Peroxo-alkane acid cooking can be mentioned as an example of acid cooking methods.

In addition to chemicals pulps, the present invention is suitable for modifying chemi-mechanical and mechanical pulps.

According to the invention, the cellulose derivative (described in the following as CMC) is introduced in liquid phase to contact the fibrous material, and the contact is continued until the cellulose derivative is bonded (sorbed) to the cellulose pulp so that it can not be washed off. The cellulose derivative can be added as solids directly to the pulp containing fibrous material, whereby the pulp is subjected to efficient dispersion to dissolve the CMC. However, it is more efficient to perform contacting by first forming a water or alkaline solution from the CMC, with the solution being mixed with the pulp containing fibrous material. This kind of solution or suspension is homogenized in room temperature or elevated temperature (<100° C.), insoluble material is separated either centrifugally or by filtration, and the clarified main solution is recovered and used for bonding.

At least 10%, preferably at least 20%, especially preferably at least 30% and most preferably at least 50% by weight of the cellulose derivative in the bonding solution, is dissolved in water or water phase in the alkaline conditions of the sorption.

When performing the invention, an essential portion of the CMC in alkaline or water solution is being subject to bonding so that at least 10% by weight, preferably at least 30% by weight, especially preferably at least 40% by weight and most preferably at least 50% by weight (or even considerably more: 60–95% by weight) of the CMC is bonded from the solution to the fibers.

During testing we noticed that sorption takes especially place, if the CMC is not too soluble in water in neutral conditions. Degree of substitution (DS) of conventional CMC grades is too high (typically for achieving sufficient bonding. Therefore, the present invention utilizes CMC grades with a DS below 0.5. In this context, the degree of substitution means the amount of substituted hydroxyl groups per anhydro-glucose unit. In neutral conditions, the water solubility of these CMC grades is about 20 weight-% at the most, preferably about 10 weight-% at the most, most preferably about 0–5 weight-%.

According to an advantageous embodiment of the invention, the used material is CMC, which is water-soluble in mainly alkaline conditions. The degree of substitution of these derivatives is, for example, about 0.2–0.3, whereby CMC is bonded in alkaline conditions, typically in pH value 8–13, or in the area of 0.3–<0.5, whereby bonding can even be accomplished in neutral conditions. Generally, the advantageous degree of substitution for the invention can be defined as about 0.2–0.4. CMC used in the invention is completely water-soluble in alkaline conditions or the alkaline solution contains only a small amount of insoluble residues causing turbidity. Generally, at least 80 weight-%, preferably at least 90 weight-% and especially at least 95 weight-% of the CMC is soluble in alkaline conditions mentioned above.

The alkaline solubility of CMC makes it possible that CMC first can be dissolved in an alkaline solution, subsequent to which the ordinary bonding can take place in essentially neutral conditions at a pH value of about 6–12, preferably about 7–10.

Another important factor controlling the bonding of CMC is its molecular weight. If the molecular weight is high, the bonding only occurs on the outer surfaces of the fibers. This kind of modification allows enhancing of the strength properties of the fibers. CMC grades with smaller molecules can, on the other hand, penetrate the internal cells of the fiber wall, which also increases the amount of bonded CMC.

According to an advantageous embodiment of the invention CMC with a degree of polymerization (DP) of about 100–5000, especially preferably about 600–4000, is used. CMC having a low DP can be bonded into the fiber in greater quantities, which can have an advantageous effect on, for example, water absorption and degree of reservation of the fiber.

Commercially available CMC grades can be used for carrying out the invention, the CMC's having a suitable degree of substitution and molar mass. When necessary, the properties of CMC can be modified in liquid phase prior to mixing it with the fibrous material in the pulp (i.e. fiber suspension). It is especially advantageous to disintegrate CMC for lowering its molar mass. In an advantageous embodiment of this option CMC is first dissolved or suspended into water or alkaline solution, subsequent to which material is added into the liquid phase for chemically or enzymatically fragmenting the anhydroglucose chain of the CMC for producing a CMC with a decreased molar mass. Examples of suitable materials include hydrogen peroxide and other radical producers. If necessary, the disintegration can be enhanced by using a catalyst.

According to an advantageous embodiment of the invention CMC is disintegrated to decrease the viscosity of its water or alkali solution. Most suitably the viscosity is decreased by at least 20%, advantageously 50–90%. Reducing the viscosity to one third produces a CMC product that bonds considerably stronger than untreated CMC.

For the bonding, the pH of the fiber suspension is set to the above-mentioned value of 6–13, preferably to 6–10. A suitable base or acid is used for setting the pH. Preferably, bicarbonate or carbonate of alkali metal or alkali metal hydroxide is used as a base. Mineral acid or an acid salt is used as the acid. Sulphuric acid and its acid salts, such as alum, are considered the most suitable salts, and sodium bicarbonate, sodium carbonate and sodium hydroxide are considered the most suitable bases.

The fiber suspension and cellulose derivative are mixed for at least 1 minute, preferably for at least 5 minutes, especially preferably for at least 10 minutes and most preferably for 20 minutes before drying (for example web forming). If a high degree of bonding is desired, mixing times of several hours, such as from 1 hour to 10 hours, are possible. Temperature is not a critical factor, in unpressurized conditions the temperature is typically 10–100° C., preferably about 20–80° C. The amount of the cellulose derivative is 0.1–5% by weight of the cellulose fibers.

As both cellulose fibers and CMC are anionic, they repel each other, whereby it is easier to achieve bonding by adding some cation to the suspension. Typically, the sodium ion (or, correspondingly, the cation) content in the bonding conditions should be more than 0.01 M, preferably more than 0.01 M and especially preferably more than 0.1 M.

The cellulose fiber suspension used for bonding can contain other fiber materials and additives, such as fillers. Calcium carbonate can be mentioned as an example of fillers. Retention promoting materials, such as sodium acetate, can be mentioned as an example of additives. The dry material content of the pulp is about 0.1–10%. The water phase of the pulp can consist of, for example, clear filtrate of the paper machine white water.

The CMC can be contacted with the cellulose fibers in any step prior to web forming. CMC can be bonded either at the pulp mill or at the paper mill. Both of these have alkaline (or essentially neutral) liquid/pulp flows, in which the bonding step can be arranged. For improving the strength properties, it is preferable to perform bonding only after beating. Further, the strength properties will be improved, if the pulp is not dried after bonding and before web forming.

In the pulp mill, the sorption can be effected in an alkaline bleaching stage, such as in oxygen (O) or peroxide (P) stage.

In the paper mill, the sorption of CMC is most suitably effected subsequent to beating of the pulp. The treated pulp is filtered and washed subsequent to sorption, before introducing the pulp to the paper machine. The filtrate and washing solutions are recirculated and, if necessary, fresh CMC feed is combined with them.

The bonding of CMC can be performed in connection with peroxide bleaching of mechanical pulps, for example in connection with manufacture of LWC papers. A typical alkali addition in the P stage is about 10–15 kg NaOH/t, i.e. about 0.3 mol/kg. The alkali can also be first used when sorpting CMC in the pulp used as strengthening pulp, and from there it can be further introduced to the P stage. If the bonding of CMC is performed in a consistency of 10%, the available alkali can increase the pH value to 12. Having the filtrate circulate around the bonding stage, even higher pH values can be attained. The alkaline filtrate used in the bonding stage can be introduced to P stage, where the CMC present in the filtrate can be sorbed on the surface of the mechanical mass, thereby increasing the bonding characteristics thereof.

The bonding of the cellulose derivative can be performed as a batch or semi-batch process or as a continuous process by first arranging the pulp retention time to be sufficiently long for the utilized process apparatus. A continuous process is considered advantageous.

The fiber pulp is formed into a web using a paper or a paperboard machine in a way known per se. Usually, the thickness of the web is 30–500 g/m$^2$. Soft tissues can be mentioned as examples of especially advantageous paper products.

The fiber suspension can also be dried for producing an absorbent fiber material used in, for example, hygiene products, such as diapers.

The amount of cellulose derivative that can be washed away from a CMC treated fibrous raw material after alkali displacement and water washing is about 10%, at the most, at a temperature of 25° C. and neutral pH conditions. CMC is not removed during beating, either. When utilizing the present invention, the strength properties can be considerably improved according to the molar mass of CMC. When compared with untreated paper, the same internal bond strength can be achieved while reducing the amount of pulp amount at least 10%.

CMC, when sorbed according to the invention, will increase the characteristic bond strength of the fibers. This means that a certain strength level can be achieved with a lower bonding level. Low bonding level, on the other hand, leads to advantageous properties, such as high opacity (printing papers) or good air permeability (packing materials). High water retention can be achieved already with a low amount of large-molecule CMC as long as the pulp is beaten before sorption.

In the following, the present invention is discussed in more detail using the following non-limiting embodiment examples.

EXAMPLE 1

Sorption of Carboxymethyl Cellulose into Pulp Fiber

CMC was sorbed into sulphate pulp, both unbeaten and PFI beaten with different revolutions. The utilized pulp was ECF bleached softwood sulphate pulp produced by Kaukaa, with dry solids content of 50%. The cold disintegration of the pulp was performed according to the standard method SCAN-C 18:65. The pulp was beaten with a PFI beater equipped and calibrated according to the standard method SCAN-C 24:67, the numbers of revolutions used were 1000, 2000, 4000 and 7000. After the beating, the Schopper-Riegler value of the pulps were determined according to the standard method SCAN-C 19:65 and the Canadian Freeness value was determined according to the standard method SCAN-C 21:65. The results are presented in table 1.

TABLE 1

SR and CF numbers for pulps beaten for different numbers of revolutions.

| PFI beating (revolutions) | SR value | CF value |
|---|---|---|
| 0 | 14.5 | 710 |
| 1000 | 15 | 680 |
| 2000 | 16 | 660 |
| 4000 | 20 | 550 |
| 7000 | 36 | 310 |

Carboxymethyl cellulose (Nymcel ZSB-10, F1226) having a substitution level of 0.20 was sorbed into the above-mentioned pulps using a rotating 8 liter pulp digester. The temperature was elevated to 60° C. in 20 minutes, and the temperature was kept at this level for an hour. pH of the sorption solution was 12.5, and the consistency of pulp used for the sorptions was 5% (50 g/l). In the beginning of the sorption the CMC content was 0.5 g/l (1% of fiber). After sorption, the pulp was cooled, filtered and washed, until its pH was 6. Reference pulps were produced in the same conditions, without the CMC addition, as the CMC treated pulps.

Figure 1:
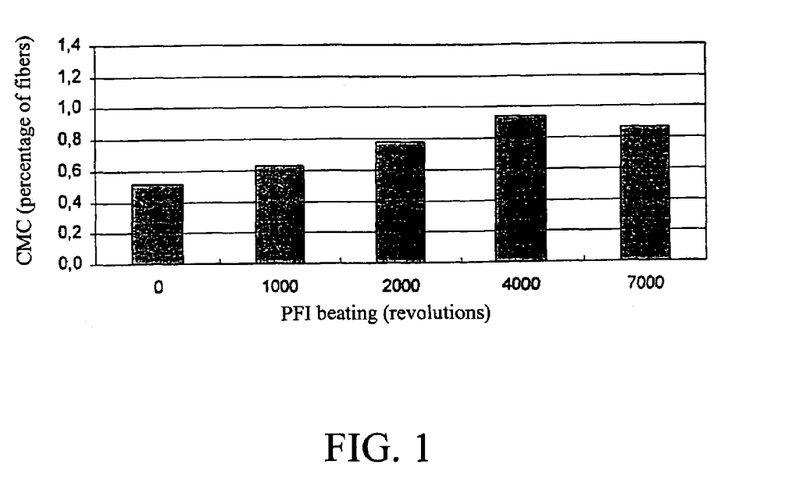
FIG. 1 illustrates the CMC content of fibers using different refining grades.

The amount of CMC sorbed into the fiber was analyzed by determining the amount of CMC present in the solution after sorption. The CMC content of the sorption solution was determined by means of a phenolsulphur acid test using a glucose standard line, and the amount of CMC present in the fibers was calculated on the basis of the CMC loss of the solution. The results are shown in FIG. 1.

As the figure shows, about a half of the used CMC (about 0.5% of fiber) was sorbed into the unbeaten fibers, and the CMC content of the fibers increased along with the beating level of the pulp, i.e. almost all of the CMC (about 1% of fiber) was sorbed into the pulp beaten for 4000 revolutions.

COMPARISON EXAMPLE

Adding Starch to the Pulp

A batch of starch-modified pulp was also produced for comparing the properties of CMC pulp. The used starch was cationic potato starch ether Raisamyl 135, with a substitution level of 0.035. The starch was introduced to the pulp as a 0.5% solution, the pulp having a consistency of 3%. The amount of starch was 0.5% of the amount of fiber. Starch was introduced both to unbeaten pulp and pulp treated with PFI beating for 4000 revolutions.

EXAMPLE 2

Testing the Pulp

Methods

1. SR and CF Values of Pulp

The Schopper-Riegler value was redetermined after treatments according to the standard method SCAN-C 19:65 and the Canadian Freeness value was determined according to the standard method SCAN-C 21:65.

2. Water Retention of Fiber

The water retention of the fiber was analyzed by means of WRV determinations according to the proposed standard method SCAN-C 102 XE (4nd proposal). WRV determinations were performed using a Jouan GR 4 22 centrifuge.

3. Drainage Properties

The drainage time of the pulp was determined using a DDA apparatus (Dynamic Drainage Analyser) manufactured by AKRIBI Kemikonsulter Ab. The used sample volume was 750 ml, the consistency of the sample was 0,6% for pulps beaten for both 1000 and 2000 revolutions; for pulps beaten for 4000 and 7000 revolutions the consistency of sample was 0,2%. The used partial vacuum was 0.14 bar. The used wire was delivered by the manufacturer, M 0,150 T 0,112.

4. Total Retention

The total retention was analysed using a DPCJ apparatus (Dynamic Paper Chemistry Jar). The sample volume was 500 ml, the consistency of the sample was 0.2%, and the agitation speed was 1000 krpm. The wire used in total retention determination was a 75 mesh wire.

Figure 2:
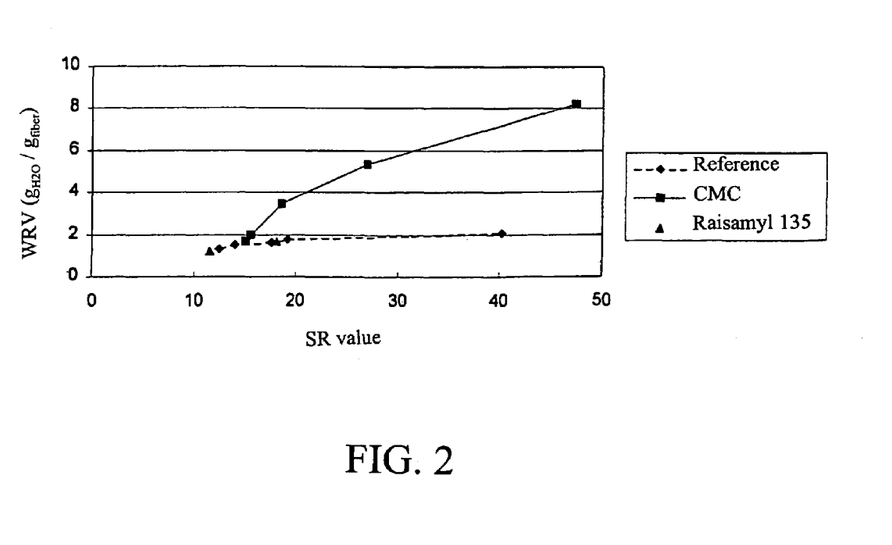
FIG. 2 illustrates the results of water retention tests.
Figure 3:
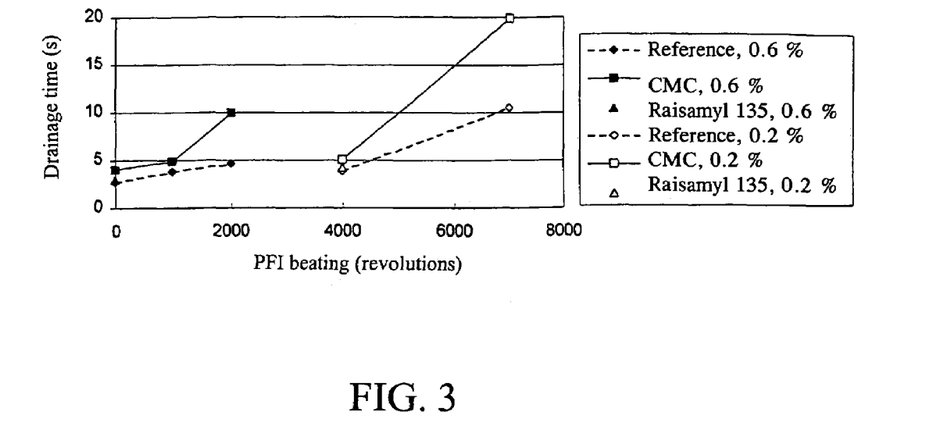
FIG. 3 illustrates the filtration times of pulp.
Figure 4:
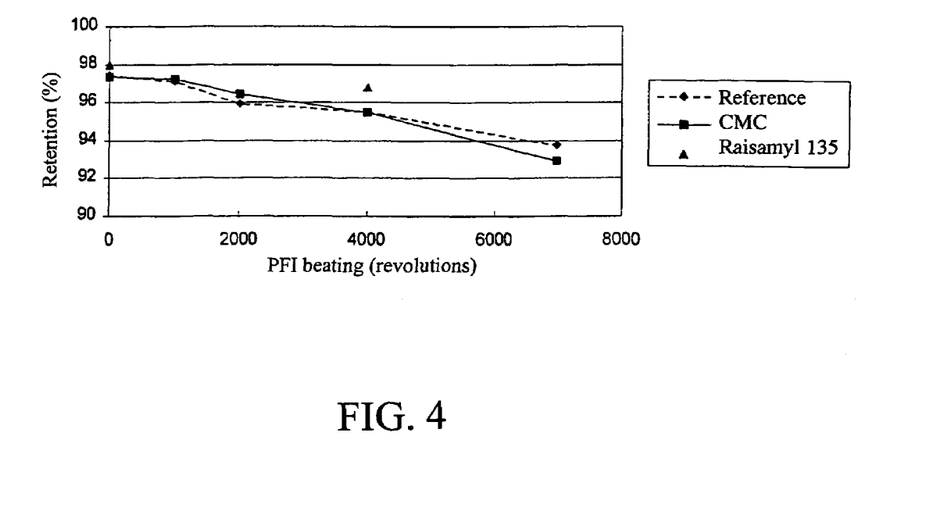
FIG. 4 illustrates the total retention of the pulp.

The results of the water retention testing are shown in FIG. 2, the drainage times of the pulp are shown in FIG. 3 and the total retention of the pulp is shown in FIG. 4.

As the appended figures illustrate, the water retention of CMC treated pulps increased considerably in proportion to the amount of beating prior to sorpting the CMC. The water retention of a CMC treated pulp beaten for 2000 revolutions was already double the retention of corresponding reference pulp. The results point to the conclusion that a CMC treated pulp beaten to a high SR value is extremely suitable for producing of, for example, soft tissues.

The drainage time given in FIG. 3 is the period of time from the start of the determination to the point when air begins to be sucked to the wire through the formed sheet. The air permeability of the formed wet sheet was measured 60 seconds after the drainage time.

FIG. 3 illustrates that CMC treated pulps were slower to drain than the corresponding reference pulps while forming a denser sheet than the reference sheets. We wish to point out at this point that even though the CMC treated pulps were thus slower to drain than the reference pulps having same beating level, the drainage was considerably faster when the tensile strength was equal.

FIG. 4 illustrates that the sorption of CMC to the pulp fibers does not have substantial effect on the retention of the pulp, but the total retentions of both the CMC treated pulps and the reference pulps beaten to a certain level were highly similar. Nevertheless, when the tensile strength levels are equal, the retention of the CMC treated pulps was better than that of the reference pulps.

EXAMPLE 3

Production of Laboratory Sheets

Laboratory sheets were produced from the pulp samples for testing the technical properties of paper. The laboratory sheets were produced without white water according to the standard method SCAN-C 26:76 with the exception of drum drying (2 h, 60° C.) and the wet pressing (490 kPa) preceding it.

The grammage, thickness and density of the paper were measured from the laboratory sheets according to the standard methods SCAN-P 6:75 and SCAN P 7:75. The results are presented in table 2.

TABLE 2

Specifications describing the common properties of the paper

| Sample | PFI beating (revolutions) | Grammage (g/m$^2$) | Thickness (μm) | Density (kg/m$^3$) |
|---|---|---|---|---|
| REF | 0 | 60.8 | 126 | 483 |
|  | 1000 | 65.2 | 117 | 559 |
|  | 2000 | 65.1 | 107 | 606 |
|  | 4000 | 62.6 | 96.6 | 648 |
|  | 7000 | 60.7 | 87.6 | 693 |
| CMC | 0 | 66.8 | 125 | 533 |
|  | 1000 | 67.3 | 110 | 611 |
|  | 2000 | 64.7 | 101 | 639 |
|  | 4000 | 64.8 | 98.6 | 657 |
|  | 7000 | 65.4 | 94.3 | 694 |
| Raisamyl | 0 | 62.9 | 128 | 492 |
|  | 4000 | 67.6 | 97.7 | 691 |

As the table describes, the densities of sheets produced from unbeaten and only slightly beaten CMC treated pulps were considerably increased when compared with the corresponding reference pulps. In the sheets produced from more extensively beaten pulps (4000 and 7000 revolutions) the density increase caused by CMC sorption was not significant.

EXAMPLE 4

Properties of Laboratory Sheets

1. Optical Properties

The optical properties of sheets produced according to example 3 (ISO lightness, opacity, light-scattering coefficient, light absorption coefficient) were determined using an Elrepho reflectometer equipped and calibrated according to the standard method SCAN-G 1:75. The measured light-scattering values Were used for calculating the relative bonded area, RBA describing the bonding level. The results are presented in table 3.

TABLE 3

Specifications describing the optical properties of the paper

| Sample | PFI beating (revolutions) | ISO lightness (%) | Opacity (%) | Light-scattering coefficient (m$^2$/kg) | RBA (%) | Light absorption coefficient (m$^2$/kg) |
|---|---|---|---|---|---|---|
| REF | 0 | 86.1 | 72.3 | 32.7 | 13.4 | 0.129 |
|  | 1000 | 85.5 | 70.5 | 27.4 | 27.4 | 0.141 |
|  | 2000 | 84.5 | 66.8 | 23.6 | 37.5 | 0.132 |
|  | 4000 | 83.7 | 62.6 | 20.6 | 45.4 | 0.140 |
|  | 7000 | 82.3 | 58.3 | 17.5 | 53.6 | 0.156 |
| CMC | 0 | 86.2 | 71.8 | 29.0 | 23.2 | 0.121 |
|  | 1000 | 84.9 | 68.5 | 24.2 | 35.9 | 0.141 |
|  | 2000 | 83.7 | 64.5 | 20.9 | 44.6 | 0.155 |
|  | 4000 | 82.6 | 61.4 | 18.2 | 51.8 | 0.164 |
|  | 7000 | 81.8 | 57.4 | 15.6 | 58.7 | 0.145 |
| Raisamyl | 0 | 86.5 | 71.6 | 30.8 | 18.4 | 0.121 |
|  | 4000 | 82.6 | 60.8 | 17.4 | 53.9 | 0.138 |

Figure 5:
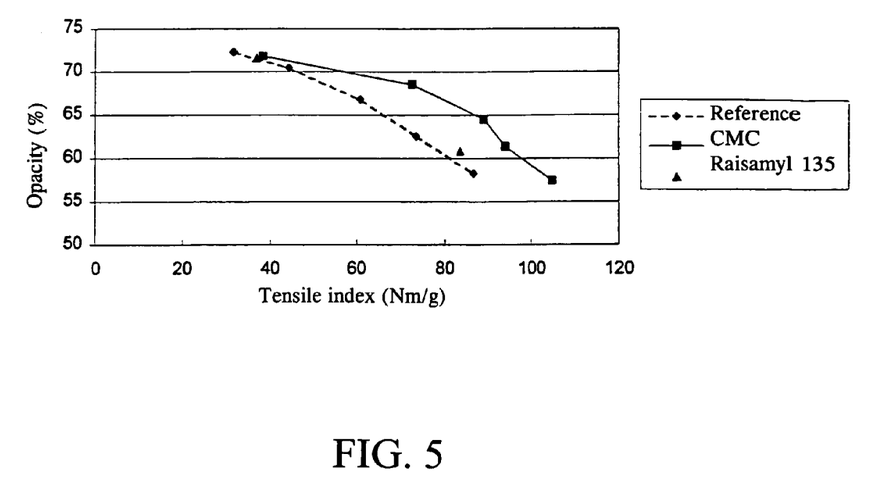
FIG. 5 illustrates the opacity of the paper as a function of tensile index.

Thus, the lightness and opacity of the sheets produced from CMC treated pulps was higher than those of the reference sheets having the same tensile strength. This is also clearly shown in the appended FIG. 5, in which opacity is shown as a function of tensile index.

2. Roughness and Air Permeability

Figure 6:
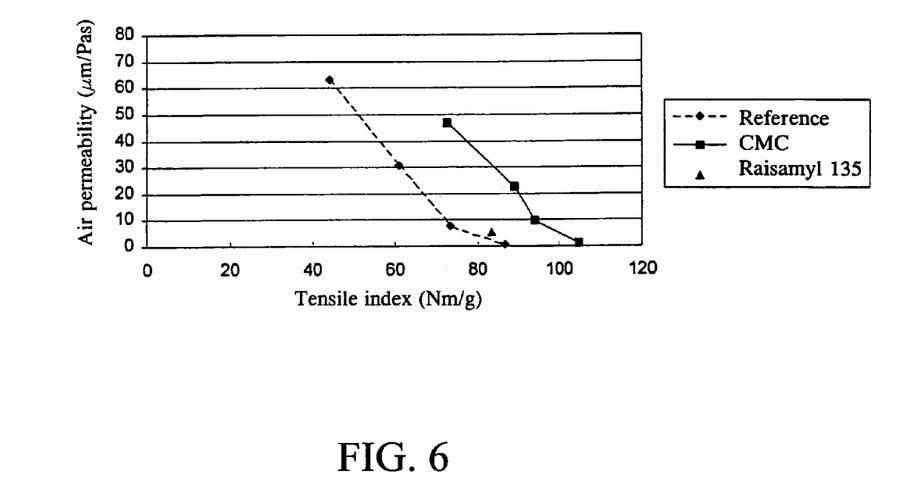
FIG. 6 illustrates the air permeability of the paper as a function of tensile index.

The roughness and air permeability of the paper were determined with a Bendtsen apparatus calibrated according to the standard method SCAN-P 21:67. The apparatus was equipped with both an air permeability measuring sensor and a roughness measuring sensor. In FIG. 6, the air permeability describing the porosity of the paper is shown as a function of tensile index. The figure illustrates that the laboratory sheets produced from CMC treated pulp having a certain tensile strength were considerably more porous than corresponding laboratory sheets produced from reference pulps.

3. Mechanical Properties

The tensile strength, stretch at break and tensile breaking load were determined using an MTS 400M —stretching apparatus, the distance between the fastening points of the paper sheet was 50 mm and the rate of elongation was 12 mm/min.

TABLE 4

Specifications describing the mechanical strength of the paper, tensile strength

| Sample | PFI beating (revolutions) | Stretch index (Nm/g) | Stretch at break (%) | Tensile breaking load (J/kg) | Tensile stiffness index (kNm/g) | Elasticity module (GPa) |
|---|---|---|---|---|---|---|
| REF | 0 | 31.7 | 3.56 | 854 | 3.53 | 1.70 |
|  | 1000 | 44.2 | 4.73 | 1487 | 3.87 | 2.15 |
|  | 2000 | 61.0 | 5.61 | 2297 | 4.32 | 2.63 |
|  | 4000 | 73.5 | 5.97 | 2933 | 5.15 | 3.33 |
|  | 7000 | 86.7 | 5.81 | 3282 | 5.89 | 4.06 |
| CMC | 0 | 38.4 | 4.54 | 1261 | 3.52 | 1.88 |
|  | 1000 | 72.7 | 6.19 | 2832 | 4.44 | 2.71 |
|  | 2000 | 89.1 | 6.03 | 3382 | 5.50 | 3.53 |
|  | 4000 | 94.2 | 6.12 | 3597 | 5.72 | 3.74 |
|  | 7000 | 105.1 | 6.02 | 3900 | 6.20 | 4.31 |
| Raisamyl | 0 | 36.9 | 4.45 | 1175 | 3.18 | 1.56 |
|  | 4000 | 83.5 | 5.98 | 3271 | 4.75 | 3.28 |

As the table illustrates, the tensile strengths of the laboratory sheets produced from CMC treated pulps were clearly higher than those of corresponding reference tensile strengths. Further, the RBA parameter (relation of bonding fiber area) was higher in the CMC treated pulps than in the reference pulps. Thus, sorption of CMC into the fibers had increased the amount of fiber bonds on a certain pulp beating level.

The tensile strengths of the sheets produced from CMC treated pulp were also considerably higher on a given bonding level than the tensile strengths of reference sheets, i.e. sorption of CMC into the fiber obviously also increased the bonding strength. Further, the stretch at break and tensile breaking load of sheets produced from CMC treated pulps were higher than those of the sheets produced from reference pulps.

4. Internal Bond Strength

The measurements of the internal bond strength were performed using an Internal Bond Tester meter. The pressure of the tape was 50 lbs/sq.in for unbeaten samples and the samples beaten for 1000 revolutions, 100 lbs/sq.in for samples beaten for 2000 revolutions, 150 lbs/sq.in for samples beaten for 4000 revolutions and 200 lbs/sq.in for samples beaten for 7000 revolutions. The results are presented in FIG. 7.

Figure 7:
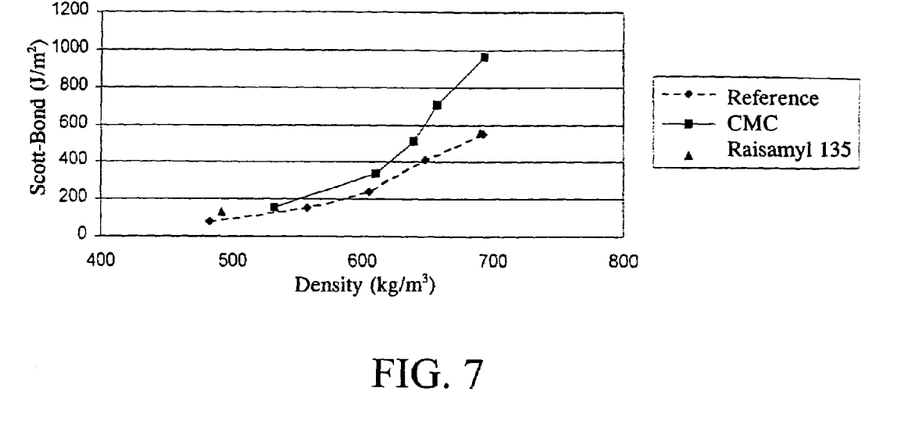
FIG. 7 illustrates the internal bond strength of the paper as a function of density.

The internal bond strengths of sheets produced from CMC treated pulps were considerably higher than the internal bond strengths of sheets produced from corresponding reference pulps, which is most probably due to the increase in characteristic bond strength caused by the sorption of CMC.

What is claimed is:

1. A method of producing a modified fiber product selected from printing paper and packaging material, according to which method
cellulosic pulp is formed into a fiber suspension which consists essentially of, as the fiber component, cellulose pulp fibers,
components modifying the properties of fibers are added to the fiber suspension and
the fiber suspension is introduced to a paper machine and formed into a web,
characterized in that
alkali soluble carboxymethylcellulose, the DS of which is 0.1 to 0.4 and the polymerization degree of which is about 600–5000, is dissolved in an alkaline solution and then mixed into the fiber suspension at alkaline conditions, and
at least 10% of the carboxymethylcellulose is bonded to the cellulose pulp fibers prior to the cellulose pulp fibers being formed into a web so that the bonded carboxymethylcellulose can not be washed off with water, to produce a modified fiber product having strength suitable for printing paper and packaging material.

2. A method according to claim 1, characterized in that the pH value of the fiber suspension is more than 8.

3. A method according to claim 1, characterized in that the fiber suspension is mixed with the alkali soluble carboxymethylcellulose for at least 5 minutes before drying.

4. A method according to claim 1, characterized in that the DS of the alkali soluble carboxymethylcellulose is 0.2–0.4.

5. A method according to claim 1, characterized in that about 10%, at the most, of the alkali soluble carboxymethylcellulose can be washed off the treated cellulose pulp fibers at a temperature of 25° C. and a neutral pH value.

6. A method according to claim 1, characterized in that in comparison with untreated paper, the same internal bond strength is achieved while using at least 10% less cellulose pulp fibers.

7. A method according to claim 1, characterized in that the alkali soluble carboxymethylcellulose is contacted with the cellulose pulp fibers in an alkaline flow of a pulp or paper mill.

8. A method according to claim 7, characterized in that the alkali soluble carboxymethylcellulose is contacted with the cellulose pulp fibers in an alkaline bleaching stage.

9. A method according to claim 8, characterized in that the alkali soluble carboxymethylcellulose is contacted with the cellulose pulp fibers in the peroxide bleaching of mechanical pulp.

10. A method according to claim 9, characterized in that the alkali soluble carboxymethylcellulose is first contacted with chemical pulp, subsequent to which the pulp is drained and the filtrate is introduced to the peroxide bleaching of mechanical pulp.

11. A method according to claim 7, characterized in that the alkali soluble carboxymethylcellulose is mixed with the cellulose pulp fibers subsequent to the beating of fibers.

12. A method according to claim 1, characterized in that the web forming is performed without an intermediate drying of the fiber suspension after bonding of the alkali soluble carboxymethylcellulose.

13. A method according to claim 1, characterized in that the amount of alkali soluble carboxymethylcellulose is 0.1 to 5% by weight of the cellulose pulp fibers.

14. A method according to claim 1, characterized in that the alkali soluble carboxymethylcellulose is allowed to be bonded to the cellulose pulp fibers from the water phase so that at least 20% of the alkali soluble carboxymethylcellulose contained by the water phase is allowed to be bonded to the cellulose pulp fibers.

15. A method according to claim 1, characterized in that the alkali soluble carboxymethylcellulose is allowed to be bonded to the cellulose pulp fibers from the water phase so that at least 30% of the alkali soluble carboxymethylcellulose contained by the water phase is allowed to be bonded to the cellulose pulp fibers.

16. A method according to claim 1, characterized in that the pH value of the fiber suspension is more than 10.

17. A method according to claim 1, characterized in that the fiber suspension is mixed with the alkali soluble carboxymethylcellulose for at least 10 minutes before drying.

18. A method according to claim 1, characterized in that the fiber suspension is mixed with the alkali soluble carboxymethylcellulose for at least 20 minutes before drying.

19. The method according to claim 1, wherein the alkali soluble carboxymethylcellulose is bonded to the cellulose pulp fibers at a pH of about 7 to 10.

20. The method according to claim 1, wherein the treated fiber suspension is filtered and washed subsequent to bonding, before introducing the fiber suspension to the paper machine.

* * * * *